United States Patent [19]

Berezkin et al.

[11] 4,148,315

[45] Apr. 10, 1979

[54] DEVICE FOR TAKING AND INJECTING MICROSAMPLES OF LIQUID

[76] Inventors: Viktor G. Berezkin, Leninsky prospekt, 40, kv. 54; Alexandr S. Bochkov, M. Kolkhoznaya ulitsa, 1, kv. 73; Vadim V. Brazhnikov, ulitsa 25 Bakinskikh komissarov, 3, kv. 327, all of Moscow; Alexei A. Artamonov, Ljubertsy, ulitsa Kirova, 45, kv. 50, Moskovskaya oblast; Leonid G. Balasanov, ulitsa Pravdy, 3/1, kv. 42, Moscow, all of U.S.S.R.

[21] Appl. No.: 813,277

[22] Filed: Jul. 6, 1977

[30] Foreign Application Priority Data

Jul. 21, 1976 [SU] U.S.S.R. .............................. 2390545

[51] Int. Cl.[2] .............................................. A61M 5/00

[52] U.S. Cl. ............................ 128/218 C; 128/218 N

[58] Field of Search ........... 128/218 R, 218 C, 218 N, 128/218 P, 221, 234, 215, 272.1, 214.4; 73/421.5; 23/252 R, 254 R; 222/386

[56] References Cited

U.S. PATENT DOCUMENTS

| | | | |
|---|---|---|---|
| 3,401,692 | 9/1968 | Harris, Jr. | 128/218 C |
| 3,677,448 | 7/1972 | Harris, Sr. et al. | 128/218 C X |
| 3,730,389 | 5/1973 | Harris, Sr. et al. | 128/234 X |
| 4,063,662 | 12/1977 | Drummond et al. | 128/218 C |

*Primary Examiner*—John D. Yasko

*Attorney, Agent, or Firm*—Steinberg & Blake

[57] ABSTRACT

A device for taking and injecting microsamples of liquid comprises a casing having a hollow needle accommodating a plunger. The end of the plunger telescoping outside the needle has a plurality of through-passing transverse bores spaced lengthwise of the plunger and having skew axes, the bores serving as cavities for successively taking a plurality of samples. The plunger is connected to a slider having a handle. The device has means for preventing the slider and plunger from rotating about the longitudinal axis.

7 Claims, 4 Drawing Figures

DEVICE FOR TAKING AND INJECTING MICROSAMPLES OF LIQUID

The invention relates to devices for taking and injecting small-volume samples ($10^{-12}-10^{-6}$ ml). The use of the device is promising in the medicine for simultaneous injection of several medical preparations which are not to be premixed in tissues and cavities of human body. The use of the invention is particularly advisable in the analytical chemistry, especially in chromatography for precision batching of microsamples and their simultaneous injection in the analytical system without premixing which is important for analysis of reactive and toxic substances.

Known in the art are various types of devices for taking and injecting microsamples of liquid in which a piston moves both in the casing and needle.

Thus, known in the art is a device for taking and injecting microsamples of liquid comprising a casing in the form of a hollow cylinder accommodating a hollow needle in which there is mounted an axially movable plunger which can be partially telescoped outside the needle. A recess is provided in that part of the plunger which may be telescoped outside the needle in operation. The recess may be of various shapes: indent, through-passing orifice and axial capillary passage, annular groove. The plunger is pointed, and the needle has a flat bevel cut. For taking a sample, the plunger which is telescoped outside the needle is placed in the liquid being sampled which fills the recess, and the plunger is then retracted back in the needle. For injecting, a sample, e.g. in the chromatography, the needle is inserted in the evaporator assembly of the chromatograph, and the plunger is telescoped outside. The liquid sample is thus removed from the recess.

The prior art devices, however, enable a sample of only one substance or a mixture of substances to be taken which, in a number of applications of such devices, such as in the reaction chromatography, represents a substantial disadvantage. Known devices cannot provide for adequate sealing of liquid sample. As a result, in dealing with highly volatile substances, the amount of substance evaporating during the time between the intake and injection of a sample is from 1 to 10% of the batched volume of sample without using additional sealing arrangements, the error being the greater the smaller the volume of sample being taken.

In addition, known devices are hard to wash for removal of substances used; efficient cleaning of surfaces of the plunger and needle from traces of analyzed substances is difficult thus resulting in contamination of subsequently taken samples with traces of preceding samples and in distortion of measurement results.

The provision in the plunger of recesses for taking samples in the form of annular grooves or capillaries at the center of the plunger requires an increased diameter of the plunger and, respectively, of the needle. It should be noted that large-diameter needles result in rapid deterioration of sealing elements of sample injection assemblies of analytical equipment.

It is an object of the invention to provide a device which enables successive intake and simultaneous injection of several different samples of liquids.

Another object of the invention is to reduce losses of liquid samples after the intake.

The invention consists in that in a device for taking and injecting microsamples of liquid comprising a casing, a hollow needle mounted to the casing, a plunger accommodated within the needle for axial movement and partial telescoping outside the needle at the front end thereof, a slider mounted in the casing, rigidly secured to the rear end of the plunger and having a handle to impart reciprocations thereto, according to the invention, the plunger is provided with a plurality of through-passing transverse bores having skew axes which serve as cavities for successively taking a plurality of samples, and there are provided means for preventing the slider and plunger from rotating about the longitudinal axis.

The provision of the plunger with several bores having skew axes enables several different samples to be taken, while means for preventing the slider and plunger from rotating about the longitudinal axis eliminate intermixing of samples. The device thus enables maximum volume of sample to be taken without enlarging the size. The spacial arrangement of the bores at an angle to one another so that traces of samples being taken cannot overlap one another in the course of reciprocations of the plunger also contributes to the prevention of intermixing of samples, hence avoids errors in the experimental results.

The use of the device enables a rapid successive injection of identical samples in pre-set quantities, which is very important in studying physico-chemical processes in the chromatography. The employment of the device enables two-threefold acceleration of intake and injection of samples.

The plunger is preferably provided with an annular groove partially extending beyond the limits of the needle when the plunger is completely telescoped outside the needle, the groove serving for taking washing liquid. The provision of this structural facility is required in view of the fact that intake and injection of several different samples of liquid result in additional difficulties in washing and cleaning the surfaces of the needle and outer periphery of the needle and outer periphery of the plunger. The provision of the annular groove brings the solution to this problem.

The slider of the device may have a plurality of locking recesses, and the casing may be provided with a spring-loaded locking member interacting with the locking recesses for locking the plunger in positions of taking samples in respective bores thereof. This is preferable in view of the provision of a plurality of bores in the plunger so that the movement of the bores relative to the needle end should be accurately controlled. The locking member enables rapid intake and injection of required number of samples without using additional measuring and synchronizing devices.

The front end of the needle is preferably cut at right angle, and the front end of the plunger terminates in a pointed tip having an annular shoulder facing the needle cut, the outside diameter of the shoulder corresponding to the outside diameter of the needle, the shoulder intimately engaging the needle cut when the plunger is completely retracted. This structural facility is preferable for two reasons. First, to have several bores in the plunger, it is desirable that the plunger diameter be as great as possible with the same normal size of the needle. The pointed tip of the plunger bearing with the annular shoulder thereof against the needle cut enables a proportional distribution of mechanical loads appearing upon penetration through a sealing member among the plunger and hollow needle. Thus the thickness of the needle walls may be substantially reduced so that the plunger diameter may be increased. Second, an additional sealing obtained due to the engagement of the shouldered portion of the tip and the needle cut enlarges the range of application of the device for taking and injecting highly volatile substances, while considerably improving reliability of the device in operation.

The invention will now be described with reference to specific embodiments thereof illustrated in the accompanying drawings, in which.

Figure 1:
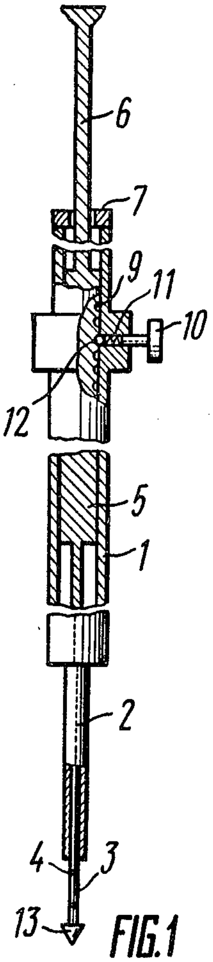
FIG. 1 is a longitudinal section of the device for taking and injecting microsamples of liquid according to the invention.
Figure 2:
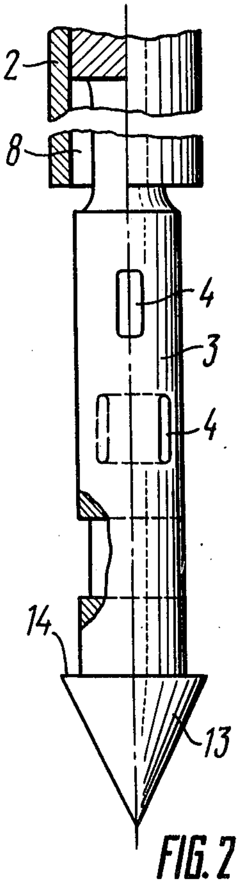
FIG. 2 is an enlarged longitudinal section of a part of the plunger body extending outside the needle when the plunger is completely telescoped outside.
Figure 3:
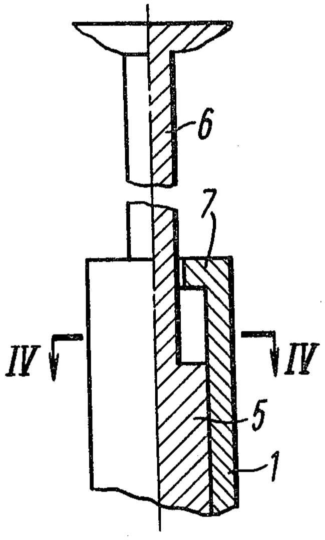
FIG. 3 is an enlarged longitudinal section of a part of the casing and slider handle.
Figure 4:
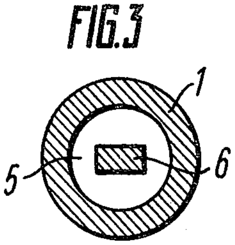
FIG. 4 is a sectional view taken along the line IV—IV in FIG. 3.

The device for taking and injecting microsamples of liquid comprises a casing 1 (FIG. 1), a hollow needle 2 mounted to the casing, a plunger 3 accommodated in the needle for axial movement and partial telescoping outside the needle 2 at the front end portion thereof. The plunger 3 has a plurality of through-passing transverse bores 4 (FIGS. 1,2) having skew axes which serve as cavities for successively taking a plurality of samples. The casing 1 accommodates a slider 5 (FIG. 1) which is rigidly secured to the rear end of the plunger 3 and has a handle 6 (FIGS. 1,3) to impart reciprocations thereto. The handle 6 comprises a faceted rod of rectangular cross-section as shown in FIG. 4, and a hole of a flange 7 (FIG. 3) of the casing 1 through which the handle 6 extends has the shape corresponding to the cross-sectional shape of the handle 6 so that the handle 6 and the respective hole of the flange 7 form means preventing the slider 5 and the plunger 3 (FIG. 1) from rotating about the longitudinal axis. The slider 5 and the needle 2 should be thoroughly lapped. The casing 1, slider 5 and handle 6 may be made of various materials including impact resistant synthetic materials.

The plunger 3 has an annular groove 8 (FIG. 2) which partially extends beyond the limits of the needle 2 when the plunger 3 is completely telescoped outside the needle 2 for taking washing liquid. The groove may vary in shape and is generally 3–5 mm high.

The slider 5 (FIG. 1) has a plurality of locking recesses 9 spaced lengthwise thereof, and the casing 1 has a spring-loaded locking member which consists of pressure screw 10, a spring 11 and a ball 12 having the diameter corresponding to the diameter of the locking recesses. The number of the recesses 9 is equal to the number of the bores 4 of the plunger 3. The spacing of the recesses 9 corresponds to the spacing of the bores 4 of the plunger 3. The locking recesses 9 may comprise annular grooves of the slider 5 or recesses of any appropriate shape.

The front end of the needle 2 is cut at right angle, and the front end of the plunger 3 telescoping outside the needle 2 terminates in a pointed tip 13 having an annular shoulder 14 (FIG. 2) facing the cut of the needle 2, the outside diameter of the shoulder corresponding to the outside diameter of the needle 2. With the plunger 3 completely retracted in the needle, the pointed tip 13 intimately engages, with the annular shoulder 14 thereof, the cut of the needle 2. The shape of the tip 13 may vary.

In operation with the device for taking and injecting microsamples of liquid, the end of the needle 2 with the retracted plunger 3 is placed in a medium being sampled, the plunger 3 is telescoped outside at a pre-set number of bores 4, and the liquid is sampled, whereafter the plunger is retracted back in the needle 2 at required number of bores 4 containing the sample taken therein. The needle 2 and the portion of the plunger 3 extending outside are washed in a solvent and dried if necessary, and then they are placed in a next liquid being sampled. For injecting a sample, the plunger 3 is telescoped outside at full length or gradually depending on conditions of experiment. The device according to the invention minimizes intermixing of samples due to the fact that the through-passing bores 4 of the plunger 3 have skew axes. The faceted handle 6 (FIG. 3) and the hole of the flange 7 prevent the slider 5 and the plunger 3 (FIG. 1) from rotating about the longitudinal axis thus also preventing the samples from intermixing. For washing the plunger 3 and the inner surface of the needle 2, the plunger 3 is telescoped completely outside, washing liquid gets in the annular groove 8 (FIG. 2), and then several reciprocations of the plunger 3 between its extreme positions are made.

The degree of telescoping of the plunger 3 outside the needle 3 is indicated by operation of the spring-loaded locking member provided in the casing 1 (FIG. 1), which cooperates with the locking recesses 9 of the slider 5. The degree of telescoping of the plunger 3 outside is determined by the number of the recesses 9 passed by the ball 12. Thus the plunger 3 may be rapidly and accurately manipulated.

In operation with the device, membranes and sealing members of sample injection assemblies of analytical equipment and containers for storing samples of liquid should be perforated. For better sealing of the system, the perforation is made by the pointed tip 13.

During the transfer of the device, the tip 13 is brought in an intimate contact with the cut of the needle 2 so as to reduce evaporation of highly volatile substances and limit the access of air oxygen to the inner space of the device.

What we claim is:

1. A device for taking and injecting microsamples of liquid comprising: a casing; a hollow needle mounted to the casing; a plunger accommodated in the needle for movement and partial telescoping beyond the limits of the needle at the front end thereof; said plunger having a plurality of bores spaced lengthwise of the plunger and arranged in such a manner as to have skew axes, the bores serving for successively taking a plurality of samples; a slider mounted in said casing and rigidly secured to the rear end of said plunger; a handle of said slide to impart reciprocations thereto; means for preventing said slider and plunger from rotating about the longitudinal axis.

2. A device according to claim 1 comprising: said plunger having an annular groove partially extending beyond the limits of said needle when the plunger is completely telescoped outside the needle, the groove serving for taking washing liquid.

3. A device according to claim 1 comprising: said plunger having a plurality of locking recesses spaced lengthwise thereof; a spring-loaded locking member mounted in said casing and cooperating with said locking recesses to lock the plunger in positions of taking samples in respective bores thereof.

4. A device according to claim 2 comprising: said slider having a plurality of locking recesses spaced lengthwise thereof; a spring-loaded locking member mounted in said casing and cooperating with said locking recesses to lock the plunger in positions of taking samples in respective bores thereof.

5. A device according to claim 1 comprising: said needle having the front end thereof cut at right angle; a pointed tip at the end of said plunger extending outside said needle; an annular shoulder of said tip facing the cut of the needle, the outside diameter of the shoulder corresponding to the outside diameter of the needle, the shoulder intimately engaging said needle cut when the plunger is completely retracted in the needle.

6. A device according to claim 2 comprising: said needle having the front end thereof cut at right angle; a pointed tip at the end of said plunger extending outside said needle; an annular shoulder of said tip facing the cut of the needle, the outside diameter of the shoulder corresponding to the outside diameter of the needle, the shoulder intimately engaging said needle cut when the plunger is completely retracted in the needle.

7. A device according to claim 3 comprising said needle having the front end thereof cut at right angle; a pointed tip at the end of said plunger extending outside said needle; an annular shoulder of said tip facing the cut of the needle, the outside diameter of the shoulder corresponding to the outside diameter of the needle, the shoulder intimately engaging said needle cut when the plunger is completely retracted in the needle.

* * * * *